United States Patent [19]

Somlo et al.

[11] Patent Number: 4,543,214
[45] Date of Patent: Sep. 24, 1985

[54] PROCESS FOR THE PREPARATION OF BROMOANTHRAQUINONES

[75] Inventors: Tibor Somlo; Johann Regli, both of Birsfelden, Switzerland

[73] Assignee: Ciba-Geigy AG, Basel, Switzerland

[21] Appl. No.: 554,650

[22] Filed: Nov. 23, 1983

[30] Foreign Application Priority Data

Jun. 23, 1983 [CH] Switzerland .................................. 3431

[51] Int. Cl.$^4$ .............................................. C07C 49/68
[52] U.S. Cl. ..................................... 260/384; 260/694
[58] Field of Search ................................. 260/384, 694

[56] References Cited

U.S. PATENT DOCUMENTS

| | | | |
|---|---|---|---|
| 3,530,151 | 9/1970 | Hoare | 260/383 |
| 3,917,723 | 11/1975 | Szczepanski et al. | 260/694 |
| 4,006,171 | 2/1977 | Majer et al. | 260/384 |
| 4,206,130 | 6/1980 | Herzog et al. | 260/384 |

FOREIGN PATENT DOCUMENTS

| | | | |
|---|---|---|---|
| 254450 | 8/1912 | Fed. Rep. of Germany | 260/384 |
| 2452014 | 5/1976 | Fed. Rep. of Germany | 260/384 |
| 28166 | of 1912 | United Kingdom | 260/384 |
| 1492137 | 11/1977 | United Kingdom | 260/384 |
| 1551585 | 8/1979 | United Kingdom | 260/384 |

Primary Examiner—Glennon H. Hollrah
Assistant Examiner—Raymond K. Covington
Attorney, Agent, or Firm—Edward McC. Roberts; Kevin T. Mansfield

[57] ABSTRACT

A process for the preparation of pure bromoanthraquinones by denitrobrominating corresponding nitroanthraquinones is described. The process comprises treating nitroanthraquinones of the formula I

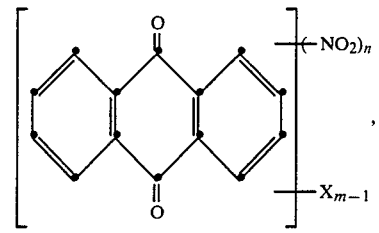

wherein X is hydroxy, mercapto, carboxy or halogen and m is 1, 2, 3 or 4 and n is 1 or 2, in the temperature range from 200° to 350° C.

Bromoanthraquinones of more than 95% purity are valuable starting materials for dye synthesis and can be used directly without further purification.

8 Claims, No Drawings

PROCESS FOR THE PREPARATION OF BROMOANTHRAQUINONES

The present invention relates to a process for the preparation of bromoanthraquinones of high purity containing $\leq 5\%$ of byproducts.

Bromoanthraquinones are important intermediates for dye synthesis. In the past, numerous processes have been developed for their preparation, including the so-called denitrohalogenation in which nitroanthraquinones are converted into the corresponding bromo- or chloroanthraquinones with bromine or chlorine (DE-OS No. 24 52 014 and DE-OS No. 24 55 587). This known process comprises using a mixture of nitroanthraquinone and a chloro- or bromoanthraquinone which acts as diluent. However, chloro- or bromoanthraquinone obtained by this method has a purity of only less than 95% and does not suffice for the direct use of these products in dye synthesis, as the reproducibility of the shade is not ensured when using such starting compounds (q.v. DE-OS No. 25 31 929 and DE-OS No. 24 58 022). In addition, the yields obtained with this process are in some cases substantially below 90% and are therefore unsatisfactory for products obtained in large-scale production.

Accordingly, it is the object of the present invention to develop an economic process which makes it possible to prepare bromoanthraquinones in high yield in a purity of over 95%. Only products which meet this purity requirement can be used directly for the production of dyes without complicated purifying operations, e.g. fractional vacuum distillation.

Surprisingly, it has now been found that bromoanthraquinones are obtained in high purity (95–99%), in a simple manner, by treating corresponding nitroanthraquinones of the formula I

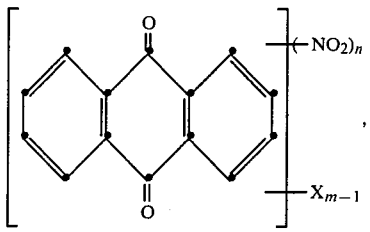

wherein X is the hydroxyl, mercapto or carboxyl group or is a halogen atom, and m is 1, 2, 3 or 4 and n is 1 or 2, with elementary bromine in the temperature range from 200° to 350° C.

The high purity of the products obtained by this process is surprising, as the denitrochlorination employing an analogous procedure yields products which contain substantial amounts of by-products which are difficult to remove, e.g. dianthraquinonyls and perchlorinated anthraquinones. In addition, the formation of such by-products increases sharply with increasing reaction temperature. As the denitrobromination requires higher temperatures than the denitrochlorination, an increased formation of impurities might have been expected. Contrary to expectations, however, the denitrobromination proceeds without noticeable formation of dimeric, polymeric or perbrominated anthraquinones. Virtually the only secondary reaction observed is the formation of phthalic anhydride; but this is not a further hindrance and can be separated without difficulty during the working up.

To obtain an easily stirrable reaction mixture and substantially to prevent the sublimation of the starting material and of the resultant bromoanthraquinone, it is advantageous to carry out the denitrobromination in the presence of an organic solvent which is inert to bromine and nitrogen oxides under the reaction conditions. The solvent is conveniently used in an amount of 1 to 500% by weight, based on nitroanthraquinone.

The use of a solvent in addition lowers the melting point of the nitroanthraquinone to be brominated. This is particularly important when using dinitroanthraquinones whose melting temperature is close to the decomposition temperature. Mononitroanthraquinones are preferably denitrobrominated in the presence of 1 to 100% by weight of solvent, and dinitroanthraquinones with advantage in the presence of 100 to 400% by weight of solvent, based on starting material.

As solvents it is preferred to use compounds which are liquid at room temperature and have a boiling point above 150° C., e.g. halogenated nitrobenzenes such as nitrofluorobenzene, nitrochlorobenzene, m-nitrobenzotrifluoride, nitrobromobenzene or dichloronitrobenzene, and also trichlorobenzene, and preferably nitrobenzene. In addition to the pure solvents, it is also possible to use mixtures of two or more solvents.

The process of this invention is carried out in the temperature range from 200° to 350° C. Below 200° C., virtually no denitrobromination takes place, or one which proceeds too slowly for large-scale production. The thermal stability of the nitroanthraquinones determines the upper temperature range. Thus, for example, 1-nitroanthraquinone slowly begins to decompose at temperatures above 370° C. It is preferred to carry out the reaction in the temperature range from 230° to 280° C.

It is convenient to use 0.5 to 1.5 mole, preferably 0.6 to 1.0 mole, of bromine per mole of nitro group to be replaced; but larger amounts of bromine can, of course, also be added. The bromine can be added to the reaction melt in liquid form, during which addition the heat of evaporation (30 kJ/mole) partly compensates for the heat of reaction of the denitrobromination. However, the bromine can also be volatilised and then introduced in gaseous form.

In the process of this invention it is preferred to denitrobrominate those nitroanthraquinones of the formula I which contain no further substituents other than one or two nitro groups, e.g. 2-nitroanthraquinone or 1,8-dinitroanthraquinone, and in particular 1-nitroanthraquinone and 1,5-dinitroanthraquinone.

When the reaction is complete, and the nitro groups are completely replaced by bromine (confirmation by thin-layer chromatography), the reaction product, optionally after cooling it to a temperature above its setting point, is charged into water or an organic solvent. For working up, the reaction product is conveniently charged into water or an organic solvent in which it is insoluble or only sparingly soluble at 20° C., and the suspension so obtained is heated to 100° C. or to the boiling point of the solvent employed. In this form of working up, by-products go into solution and the desired bromoanthraquinone is obtained in pure form as a readily filterable granulate. In addition to water, suitable organic solvents are: alcohols such as methanol, isopropanol or also higher alcohols; aromatic hydrocarbons such as toluene, xylene or nitrobenzene; aliphatic hydrocarbons such as the mixtures of isoparaffins which have a boiling range from 150° to 210° C. and are sold for example by ESSO under the registered trademark Isopar ®; and also ketones such as methyl ethyl ketone or methyl isobutyl ketone.

If the melt is charged into water or a lower boiling alcohol, bromoanthraquinones of 96 to 98% purity are obtained. If solvents such as xylene, chlorobenzene, dichlorobenzene or nitrobenzene are used, then bromoanthraquinones of up to 99% purity are obtained. It is, of course, possible to dissolve the hot reaction melt in a suitable solvent from which the bromoanthraquinone crystallises in pure form, e.g. chlorobenzene or dichlorobenzene. Further, if the denitrobromination is carried out in the presence of larger amounts of solvent, using e.g. the same amount of solvent as of nitroanthraquinone, then the hot reaction mixture is slowly cooled to room temperature or to 0° C., whereupon the product precipitates in crystalline form in 98–99% purity.

The process of this invention can be carried out batchwise or continuously. The batchwise process is carried out e.g. in the following manner:

The nitroanthraquinone compound, e.g. 1-nitroanthraquinone, optionally together with an inert organic solvent, is charged into a reactor with heating jacket and equipped with reflux cooler, waste gas absorption unit and stirrer, and heated to a temperature in the range from 230° to 280° C. A low viscosity melt is formed. With efficient stirring, bromine is then introduced, the rate of addition being conveniently so chosen that gentle bromine reflux is maintained in the condenser. After a reaction time of about 3 to 10 hours, no more bromine is consumed and the presence of nitroanthraquinone can no longer be detected in a thin-layer chromatogram. For working up, the reaction mixture is cooled to a temperature of about 200° C. and then, with efficient stirring, discharged into the same or into the two-fold amount of water to form a suspension. This supension is subsequently refluxed for about 1 hour, in the course of which time by-products go into solution. After cooling and filtration, the isolated solid is washed with hot water and dried in vacuo, affording the corresponding bromoanthraquinone, in this case 1-bromoanthraquinone, in a yield of over 95% in 96 to 97% purity.

The invention is illustrated by the following Examples, in which parts and percentages are by weight.

EXAMPLE 1

A 1 liter double mantle flask equipped with propeller or anchor stirrer, bromine inlet with metering pump, and reflux condenser attached to a waste gas adsorption unit, is charged with 1265 parts by weight of 1-nitroanthraquinone and 60 parts by weight of nitrobenzene. The mixture is heated to 240° C. and, at this temperature and with efficient stirring, elementary bromine is pumped in by means of the metering pump. The rate of addition is so chosen that gentle bromine reflux is always maintained in the reflux condenser. After about 200 to 220 ml of bromine have been added over 10 hours, no more bromine is taken up by the reaction mixture and the presence of 1-nitroanthraquinone can no longer be detected in a thin-layer chromatogram. The mixture is then cooled to 200° C. and the melt is discharged through the bottom outlet into 2 liters of vigorously stirred water. The resultant suspension is then refluxed and nitrobenzene is separated in a water separator. After about 1 hour the suspension is cooled to about 80° C., filtered, and the filter cake is washed with hot water and dried in vacuo at 120° C., affording 1400 parts by weight of 1-bromoanthraquinone in 96–97% purity. The yield, based on 1-nitroanthraquinone, is 97.5%.

EXAMPLE 2

1265 parts by weight of 1-nitroanthraquinone and 30 parts by weight of 1,4-nitrobromobenzene are heated to 275° C. in a laboratory apparatus as described in Example 1 and, at this temperature, elemental bromine is added such that a very gentle bromine reflux is constantly maintained in the condenser. After about 190 ml of bromine have been added over about 3 hours, no more bromine is taken up by the reaction mixture and the presence of 1-nitroanthraquinone can no longer be detected in a thin-layer chromatogram. The mixture is then cooled to 200° C. and discharged into 1.5 liters of well stirred nitrobenzene. The suspension is again heated to 150° C. and almost all of the 1 bromoanthraquinone goes into solution. On cooling, the product precipitates in large dark yellow crystals. These crystals are isolated by filtration, washed with a small amount of nitrobenzene and dried in vacuo at 120° C., affording 1320 Parts by weight of 1-bromoanthraquinone in 99.5 to 100% purity. The yield, based on 1-nitroanthraquinone, is 92%.

EXAMPLE 3

1265 parts by weight of 2-nitroanthraquinone are reacted at 270° C. with elemental bromine in the presence of 60 parts by weight of nitrobenzene in a laboratory apparatus as described in Example 1. When the reaction is complete, the melt is discharged into 2,000 parts by weight of vigorously stirred methanol at 200° C. The suspension so obtained is refluxed for 1 hour, cooled to 50° C., filtered and dried, affording 1390 g of 2-bromoanthraquinone (97% yield) in 98% purity.

EXAMPLE 4

3300 parts of nitrobenzene are charged into an enamel reactor equipped with high temperature heating unit, multiple coil condenser, bromine inlet pipe and condenser connected to a gas adsorption unit, and then 3290 parts of 1-nitroanthraquinone are stirred in as approximately 98% product. The mixture is heated to 245° C., giving rise to a slight overpressure (0.5 to 0.7 atmos.), which is maintained by means of a pressure regulator to reach the required reaction temperature. Then 1800 parts of bromine are added to the reaction mixture at 245°–250° C. over 10 to 12 hours. The rate of addition is controlled such that gentle bromine reflux is constantly maintained in the condenser. The reaction is complete when almost no more bromine is taken up and a chromatogram shows that the amount of 1-nitroanthraquinone present has fallen to less than 1%.

The mixture is then cooled to 170° C., briefly blown out with nitrogen, and discharged into a crystallisation tank. The reaction mixture is cooled to 20° C. (or 0° C., as required) by means of a temperature programme, and the crystals are filtered with suction and washed with 2 to 3×500 parts of nitrobenzene.

The filter cake, which still contains nitrobenzene, is further processed or dried. Yield: about 3400 parts of 1-bromoanthraquinone in 98–99% purity=3350 parts of 100% 1-bromoanthraquinone (90% of theory) based on 1-nitroanthraquinone.

The mother liquor, about 3500 kg, is distilled, the nitrobenzene is reused, and the distillation residue is incinerated. The nitrobenzene washing can be re-used without purification.

EXAMPLE 5

An enamel reactor is charged with 750 parts of nitrobenzene and then 750 parts of 100% nitroanthraquinone are added as approximately 98% product, with stirring, to the solvent. The mixture is heated to 245° C. and then 300 parts of bromine are introduced at 245°–250° C. under slight overpressure (0.5 to 0.7 atmos.) over about 5 hours. A suspension of 254 parts of 1-nitroanthraquinone in 254 parts of nitrobenzene and simultaneously 150 parts of liquid bromine are added, under pressure, to the reaction mixture each hour over 10 hours. When the addition of 1-nitroanthraquinone is complete, another 20 parts of liquid bromine are added, under pressure, each hour until almost no more bromine is taken up and a thin-layer chromatogram shows that the amount of 1-nitroanthraquinone has fallen to less than 1%. The mixture is subsequently cooled to 170° C., briefly blown out with nitrogen, and discharged into a crystallisation tank, where it is cooled to 20° C. (or to 0° C., as required) by means of a temperature programme. The crystals are filtered with suction and washed with 2 to 3×500 parts of nitrobenzene. The yield and quality of the product are in accord with Example 4.

EXAMPLE 6

An enamel reactor is charged with 750 parts of nitrobenzene and 750 Parts of 100% 1-nitroanthraquinone as 98% product are added, with stirring, to the solvent. The mixture is heated to 220° C. and a further 1550 parts of 1-nitroanthraquinone are added. The mixture is then heated to 240° C. and 1200 parts of bromine are introduced at 240°–245° C. over 10 hours. The rate of addition is so regulated that gentle reflux is constantly maintained in the condenser. Then 335 parts of 1-nitroanthraquinone and 187 parts of bromine are added each hour over 7 hours to the reaction mixture at 240°–245° C. (total of 2345 parts of 1-nitroanthraquinone and 1309 parts of bromine). When the addition of 1-nitroanthraquinone is complete, another 20 parts of bromine are added each hour until almost no more bromine is taken up and a thin-layer chromatogram shows that the amount of 1-nitroanthraquinone present has fallen to less than 1%.

Upon completion of the reaction, the reaction mixture is cooled to 200° C., briefly blown out with nitrogen, and 5103 parts of the 6043 parts of melt are discharged, with efficient stirring, into a vessel containing 4600 parts of chlorobenzene. The mixture in the vessel is heated to reflux (130° C.) to give a clear reddish brown solution. The solution is cooled and the product crystallises in the form of yellow needles. These crystals are are isolated by filtration at 20° C., washed with 1000 parts of chlorobenzene in several portions and dried, affording 1-bromoanthraquinone in about 98% purity and in a yield of about 90% of theory.

About 940 parts of melt remain in the initial reactor. To this melt are added 335 parts of 1-nitroanthraquinone and 187 parts of bromine each hour over 15 hours at 245°–250° C. (total of 5025 parts of 1-nitroanthraquinone and 2805 parts of bromine). When the addition of 1-nitroanthraquinone is complete, another 20 parts of bromine are added each hour until almost no more bromine is taken up and a thin-layer chromatogram shows that the amount of 1-nitroanthraquinone present has fallen to less than 1%. When the reaction is complete, the reaction mixture is cooled to 200° C., briefly blown out with nitrogen, and 5506 parts of the 6446 parts of melt are discharged into a vessel containing 5700 parts of chlorobenzene. The mixture is heated briefly to reflux, then cooled to 20° C. The crystals are isolated by filtration, washed with chlorobenzene and dried.

EXAMPLE 7

In an apparatus as described in Example 1, 1265 parts pf 1-nitroanthraquinone are melted by heating to 240° C. and then elemental bromine is pumped in, with efficient stirring, at 245°–250° C. The rate of addition is so chosen that gentle bromine reflux is constantly mantained in the reflux condenser. After about 624 parts of bromine have been added over about 10 hours, no more bromine is taken up by the reaction mixture and the presence of 1-nitroanthraquinone can no longer be detected in a thin-layer chromatogram. The mixture is cooled to 200° C. and the melt is discharged into 1200 parts of efficiently stirred chlorobenzene. The resultant suspension is cooled to 20° C. and filtered. The filter cake is washed with chlorobenzene and the crystals are dried in vacuo at 120° C., affording 1350 parts of 1-bromoanthraquinone in 99–99.5% purity. The yield, based on 1-nitroanthraquinone, is 96%.

EXAMPLE 8

6.5 parts of 1-nitroanthraquinone, which has been melted by heating to 250°–260° C., are charged per hour into the top of a 2 meter bubble cap column of 100 mm diameter and containing 10 sieve trays. To this melt are added, in counter-current, 3 parts per hour of bromine which has been volatalised and heated to 240° C. in an evaporator. On flowing through the column, the 1-nitroanthraquinone is converted completely into 1-bromoanthraquinone, which exits from the column via a siphon and is discharged into efficiently stirred water. The aqueous suspension is filtered at about 80° C. and the product is washed with hot water and dried in vacuo at 120° C., affording 1-bromoanthraquinone in 96–97%. The yield, based on 1-nitroanthraquinone, is 97.5%.

EXAMPLE 9

450 parts of nitrobenzene and 300 parts of 1,5-dinitroanthraquinone are heated to 260° C. in a pressure reactor (for overpressure up to 3 atmos.) which is equipped with a pressure regulator by means of which waste gases are able to escape under an adjustable slight overpressure. In the course of this heating an overpressure of about 1.2 atmos. forms. While maintaining the same temperature and overpressure, 240 parts of bromine are pumped into the mixture over about 8 hours. The waste gases escape through the pressure regulator. When no more bromine is taken up by the reaction mixture and the presence of neither 1,5-dinitroanthraquinone nor 1-bromo-5-nitroanthraquinone can be detected in a thin-layer chromatogram, the mixture is cooled to 200° C., blown out with nitrogen, and cooled to 20° C. with an optimum temperature programme for the crystallisation.

The dense crystal slurry is discharged onto a suction filter and filtered. The filter cake is washed with nitrobenzene and dried, affording 360 parts (98% of theory) of chromatographically pure 1,5-dibromoanthraquinone.

What is claimed is:

1. A process for the preparation of pure bromoanthraquinones by denitrobrominating corresponding nitroanthraquinones, which process comprises treating nitroanthraquinones of the formula I

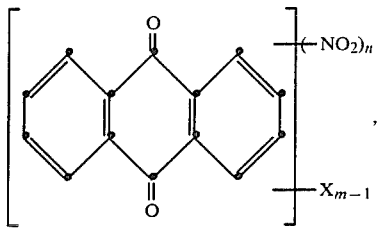

wherein X is hydroxy, mercapto, carboxy or halogen, m is 1, 2, 3 or 4 and n is 1 or 2, with elementary bromine in the temperature range from 200° C. to 350° C.

2. A process according to claim 1, wherein the denitrobromination is carried out in the presence of an inert organic solvent with a boiling point of >150° C.

3. A process according to claim 2, wherein 1 to 500% by weight of solvent is used, based on nitroanthraquinone.

4. A process according to claim 2, wherein the solvent employed is a halogenated nitrobenzene or nitrobenzene.

5. A process according to claim 1, which is carried out in the temperature range from 230° to 280° C.

6. A process according to claim 1, wherein 0.5 to 1.5 moles, preferably 0.6 to 1 mole, of elementary bromine are used per mole of nitro group.

7. A process according to claim 1, wherein 1-nitroanthraquinone or 1,5-dinitroanthraquinone is denitrobrominated.

8. A process according to claim 1, comprising the further step of charging the melt of the reaction product into water or an organic solvent in which it is insoluble or only sparingly soluble at 20° C., and, if appropriate, heating the resultant suspension to boiling temperature.

* * * * *